United States Patent [19]

Sandock

[11] Patent Number: 5,609,573
[45] Date of Patent: Mar. 11, 1997

[54] ELECTROSURGICAL SUCTION/IRRIGATION INSTRUMENT

[75] Inventor: Paul Sandock, New Hartford, N.Y.

[73] Assignee: Conmed Corporation, Utica, N.Y.

[21] Appl. No.: 608,330

[22] Filed: Feb. 28, 1996

[51] Int. Cl.$^6$ ................................................. A61B 17/20
[52] U.S. Cl. ............................. 604/22; 604/30; 604/35; 606/37; 606/42
[58] Field of Search ................ 128/749–58; 604/19, 604/22, 27, 30, 32–6, 38–9, 264.6, 294; 606/32, 39, 41–2, 45–6, 167–6, 169–73, 179–80

[56] References Cited

U.S. PATENT DOCUMENTS

| | | | |
|---|---|---|---|
| 4,936,842 | 6/1990 | D'Amelio et al. | 606/42 |
| 5,174,300 | 12/1992 | Bales et al. | 128/751 |
| 5,219,348 | 6/1993 | Buess et al. | 606/32 |
| 5,273,524 | 12/1993 | Fox et al. | 604/21 |
| 5,295,956 | 3/1994 | Bales et al. | 604/30 |
| 5,429,596 | 7/1995 | Arias et al. | 604/34 |
| 5,439,005 | 8/1995 | Vaughn | 128/755 |
| 5,468,240 | 11/1995 | Gentelia et al. | 606/42 |

*Primary Examiner*—Corrine M. McDermott
*Assistant Examiner*—Ellen Tao
*Attorney, Agent, or Firm*—Larson & Taylor

[57] ABSTRACT

An electrosurgical device provides the electrical energy from an electrosurgical generator to an electrode for cutting, coagulation, and the like, and further provides suction and irrigation to a cannula for the electrode. The device comprises a handle assembly adapted to be held in the hand of a user. The handle assembly is connected to suction and irrigation supplies as well as to the electrosurgical generator. An instrument port at the distal end of the handle assembly has a finger wheel for rotating the instrument port in relation to the handle assembly. Cutting and coagulation current are controlled by thumb switches located on the proximal side of the handle assembly. Suction and irrigation are controlled by thumb actuated buttons also located on this proximal side. A safety switch disconnects the cutting or coagulation current from the instrument port when either the suction or the irrigation button is actuated. The cannula is connected to the handle assembly at the instrument port using a leakage free connector.

8 Claims, 4 Drawing Sheets

ELECTROSURGICAL SUCTION/IRRIGATION INSTRUMENT

FIELD OF THE INVENTION

The present invention relates generally to electrosurgical instruments, and more particularly to a reliable, inexpensive, safe, and efficient electrosurgical instrument having suction and irrigation capabilities for use during endoscopic procedures.

BACKGROUND OF THE INVENTION

Typically, during electrosurgery, an electrosurgical generator provides a high frequency or radio frequency signal to a hand-held surgical electrode having a thin knife-like tip which is applied to a patient. The patient is grounded to the generator via a patient ground plate. The relatively small area of contact by the electrode with the patient provides an intense current in a highly localized area, producing a cutting action. This current then passes through the patient's body to the patient ground plate wherein the area of contact is large enough that no burning effect occurs at this location.

To produce this cutting action, the generator is activated to produce a continuous signal, typically a sine wave signal. The same instrument may also be applied to the wound after cutting in order to produce coagulation. This coagulation is produced by a pulsing signal from the generator. Switching means are thus needed to enable the operator to switch between the two types of electrical energy produced by the generator.

Although a number of arrangements have been devised for selectively activating the electrical energy, the most satisfactory of these arrangements is a multiple wire cable conductor extending from the generator to the hand-held electrode. One conductor is normally connected to the electrode to carry the therapeutic current (cutting or coagulating) and two other conductors are selectively connectable to the therapeutic current conductor through switches to complete circuits back to the activating means for causing the generator to produce the desired mode of current.

For use during endoscopic surgery, surgical instruments, including electrosurgical instruments, typically are provided with elongated barrel members that may be directed through an appropriately sized trocar tube. In these types of instruments, it is well known in the art to provide suction and irrigation capabilities in addition to the electrosurgical therapeutic current capabilities so that several functions may be provided through one trocar tube. Also, in these type of instruments, because the electrode tip is located at the end of an elongated device, it can be difficult to accurately control. Therefore, a pistol grip handle is often used to provide more accurate control.

One such instrument is disclosed in U.S. Pat. No. 5,273,524 to Fox et al. (Fox). The Fox patent discloses an electrosurgical instrument having an elongated barrel member attached to a handle member. Therapeutic current (cutting or coagulating) is provided to an electrode which is selectively extended from a sheath at the distal end of the barrel member. Push buttons located on the back of the handle member selectively connect either suction or irrigation to the barrel member and the push buttons control this selection by pinching the respective suction or irrigation tube when the button is in the released position and releasing the tube as the button is depressed.

U.S. Pat. No. 5,295,956, to Bales et al. (Bales) discloses an endoscopic instrument which provides cutting or coagulating current to an electrode which is located axially within an elongated cannula and protrudes from the distal end of the cannula. One of a variety of electrodes is inserted into the instrument through the back of the handle. Current to the electrode is activated by thumb switches that are located on the back of the handle. Two triggers are provided on the front side of the handle and are actuated by the user's fingers for selectively providing suction or irrigation to the cannula. Similarly to the buttons in the Fox patent, in the released position, each trigger pinches a tube that supplies either suction or irrigation to the cannula and, in the depressed position, each trigger releases its respective tube, allowing either suction or irrigation to reach the cannula. The Bales patent also discloses a safety switch which disconnects the electrical connection between the current supply cable and the electrode when either of the switches is depressed, i.e., when suction or irrigation is being used, so as to prevent burns and shocks to the patient. Variable suction strength is provided to the end port of the cannula by a sleeve which slidingly engages the cannula and is moved longitudinally to selectively expose lateral holes at the proximal end of the cannula.

U.S. Pat. No. 4,936,842 to D'Amelio et al. (D'Amelio), discloses an electrosurgical instrument wherein a bipolar electrosurgical probe is rotatably connected to a handle portion. Rotation of the probe with respect to the handle portion allows the surgeon to position the active portion of the probe as needed.

While the instruments disclosed in the prior art provide useful features, these features have not been implemented in the most effective, safe, reliable, and efficient manner.

SUMMARY OF THE INVENTION

In accordance with the present invention, an effective, safe, reliable and efficient electrosurgical device is provided having the capability to provide electrical energy from an electrosurgical generator to an electrode for cutting, coagulation, and the like and, further, to provide suction and irrigation to a cannula.

In a preferred embodiment the electrosurgical device comprises a handle assembly adapted to be held in the hand of a user, having a proximal side and a distal side. The handle assembly comprises a suction port coupled to a suction supply, an irrigation port coupled to an irrigation supply, an instrument port located on the distal side of the handle assembly having a finger wheel for rotating the instrument port in relation to the handle assembly, the finger wheel being located such that complete 360 degree rotation may be easily accomplished with a finger of the user's hand. Further, the handle assembly comprises suction valve means, actuated by a suction button located on the proximal side of the handle assembly so as to be easily depressed with the thumb of said user's hand, for selectively coupling, in fluid communication, the suction port to said electrode port, and an irrigation valve means, actuated by an irrigation button, also located on the proximal side of said handle assembly, so as to be easily depressed with the thumb of said user's hand, for selectively coupling, in fluid communication, the irrigation port to the instrument port.

Also provided is a cable having three conductors. The first conductor carries therapeutic current from the electrosurgical generator and is electrically coupled to the instrument port through a safety switch which is actuated by depression of either the suction button or the irrigation button to decouple the conductor from the instrument port. The second conductor carries an actuating signal to the electrosurgical generator from a cutting switch which is located on the proximal side of the handle assembly and the third conductor carries an actuating signal to the electrosurgical generator from a coagulation switch which is located next to the cutting switch.

The location of the buttons and switches in the present invention has several advantages over the prior art. Since all four buttons and switches are located on the proximal side of the handle assembly, they may each easily be actuated with the user's thumb. This type of actuation allows more accurate control of the elongated instrument because the user supports the device with his palm and his fingers while depressing a button or switch with his thumb. Also, since only one digit is used to depress any of the buttons or switches (unlike the Bales patent which uses both thumb actuated buttons on the proximal side of the handle and finger actuated triggers on the distal side of the handle) there is a decreased likelihood of actuating more than one button or switch simultaneously.

Also advantageously, connections to the instrument port are effected such that suction/irrigation or therapeutic current may be provided to the instrument port even while it is being rotated.

The handle assembly is a universal type handle assembly and, as such, may accept one of several instruments as an attachment through the instrument port and has the capability to provide the attached instrument with cutting or coagulation therapeutic current and suction/irrigation. Advantageously, the attached instrument may be an elongated instrument for providing action to a patient through a trocar tube. For example, an elongated cannula may be attached to the handle assembly to provide suction/irrigation to a patient, or, an elongated electrode may be attached to provide therapeutic current to a patient. In a preferred embodiment, an instrument is provided having an elongated cannula in combination with an elongated electrode for providing both suction/irrigation and therapeutic current to a patient through a trocar tube.

Also, in a preferred embodiment, the instrument assembly is attached to the instrument port of the handle assembly in a manner which allows quick, positive, leakage free attachment and easy detachment. The instrument assembly is further provided with a insulating sleeve for covering the conductive cannula. This sleeve slides between an extended position, wherein the cannula and the electrode tip are covered, and a retracted position, wherein only the cannula is covered. This is particularly advantageous for protection of body tissue during insertion of the instrument through the trocar tube. The sleeve is attached to a sleeve grip for moving the sleeve between the retracted (proximal) and the extended (distal) position and the sleeve may also be moved from the extended position to the retracted position by inserting the instrument into the trocar tube and urging the sleeve grip proximally with the rim of the trocar tube.

DETAILED DESCRIPTION OF THE PREFERRED EMBODIMENTS

Figure 1:
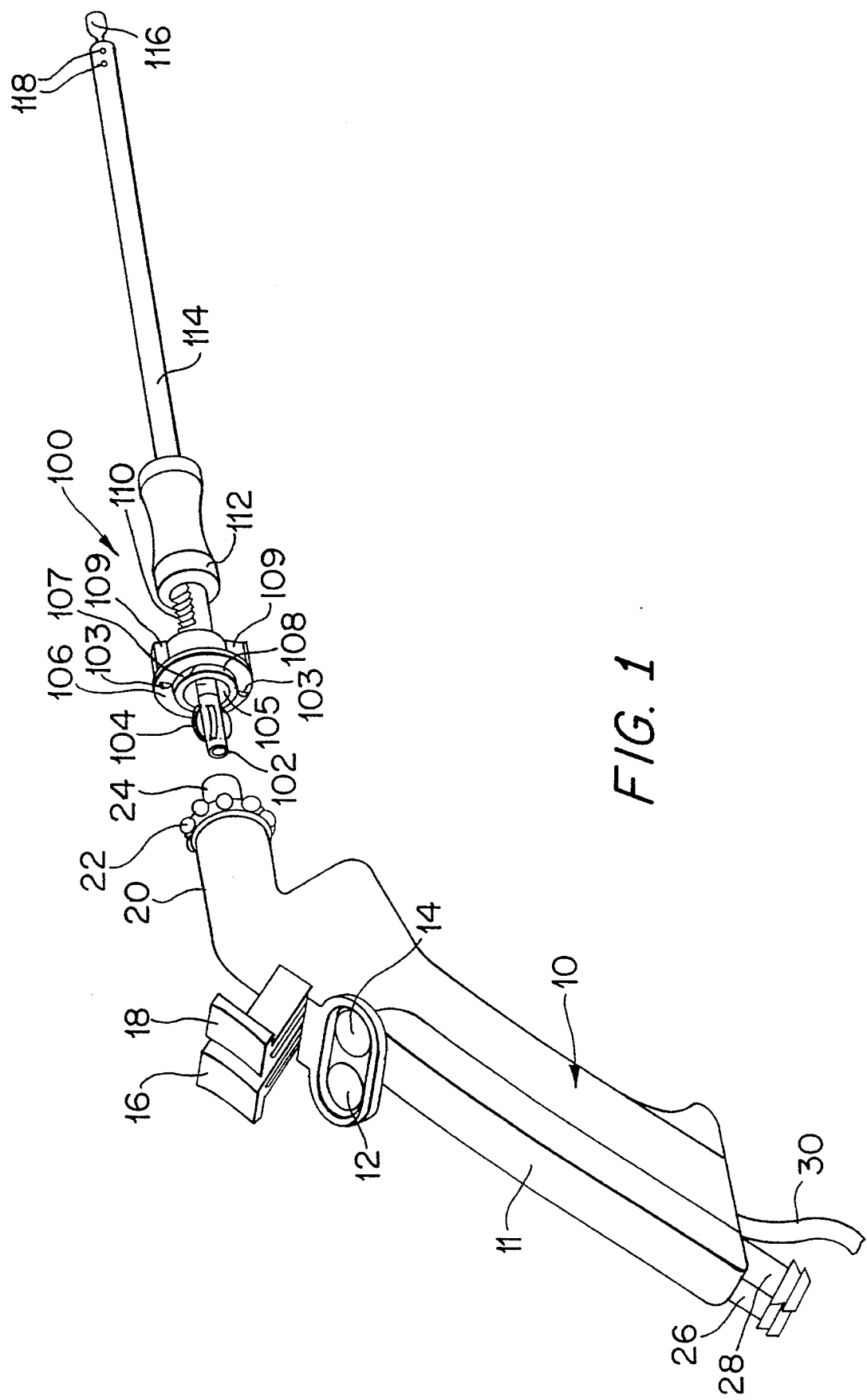
FIG. 1 is a partially exploded perspective view of a preferred embodiment of the electrosurgical device of the present invention.

With reference now to the drawings in which like numerals represent like elements throughout the several views, FIG. 1 shows a perspective view of a preferred embodiment of an electrosurgical device of the present invention. A handle assembly 10 is shown having a handle shell, and a cutting switch 12 and a coagulation switch 14 located on the back or proximal side of handle assembly 10. A suction button 6 and an irrigation button 18 are located just above cutting switch 12 and coagulation switch 14 such that the user may grip handle assembly 10 in the palm of the hand and may easily depress a selected one of the buttons or switches with the thumb while the handle is stably supported by the fingers. Finger wheel 22 having instrument port 24, located at the nose 20 of handle assembly 10, rotates with respect to nose 20 and is located such that it may easily be rotated with the index finger of the same hand used to hold handle assembly be. Suction tube 26 and irrigation tube 28 enter handle assembly 10 as shown and suction tube 26 and irrigation tube 28 selectively communicate with instrument port 24 upon depression of suction button 16 or irrigation button 18, respectively. Cable 30, which is connected to an electrosurgical generator (not shown) enters handle assembly 10 and contains three conductor wires. One conductor is connected to cutting switch 12, a second conductor is connected to coagulation switch 14 and a third conductor is a common conductor which carries the therapeutic current and, in use, is connected to electrode tip 116.

An instrument assembly 100 is shown having a stainless steel cannula 102 running longitudinally therethrough with an electrode tip 116 being rigidly and electrically connected to cannula 102 at the distal end of cannula 102. A spring connector 104 is also stainless steel and is mounted on the proximal end of cannula 102 such that spring connector 104 is electrically connected to electrode tip 116 via cannula 102. A connector 106, having a face 107, a threaded portion 108, wings 109, and a ratchet post 110, surrounds and is rigidly connected to cannula 102. Lock-bumps 103 are located on face 107 of connector 106. Connector 106 is made out of a nonconductive material (such as plastic) and is used to connect instrument assembly 100 to handle assembly 10. A sleeve grip 112 slides longitudinally on ratchet post 110 and is selectively positionable on ratchet post 110 by engaging detents on ratchet post 110. A sleeve 114 is connected to sleeve grip 112 such that sleeve 114 may be extended distally to cover electrode tip 116 or retracted proximally to expose electrode tip 116. Sleeve 114 is shown in a partially extended position in FIG. 1 and in the retracted position in FIG. 4. Holes 118 are located through sleeve 114 at its distal end for side venting of suction.

In use, instrument assembly 100 is connected to handle assembly 10, suction tube 26 is connected to a suction source and, when suction button 16 is depressed, suction tube 26 is in communication with cannula 102. Irrigation tube 28 is connected to an irrigation source and, when irrigation button 18 is depressed, irrigation tube 28 is in communication with cannula 102. Further, when cutting switch 12 is actuated, cutting current is supplied to electrode tip 116 and when coagulation switch 14 is actuated, coagulation current is supplied to electrode tip 116. However, as will be discussed below, when either suction button 16 or irrigation button 18 is depressed, no current may be supplied to electrode tip 116.

Figure 2:
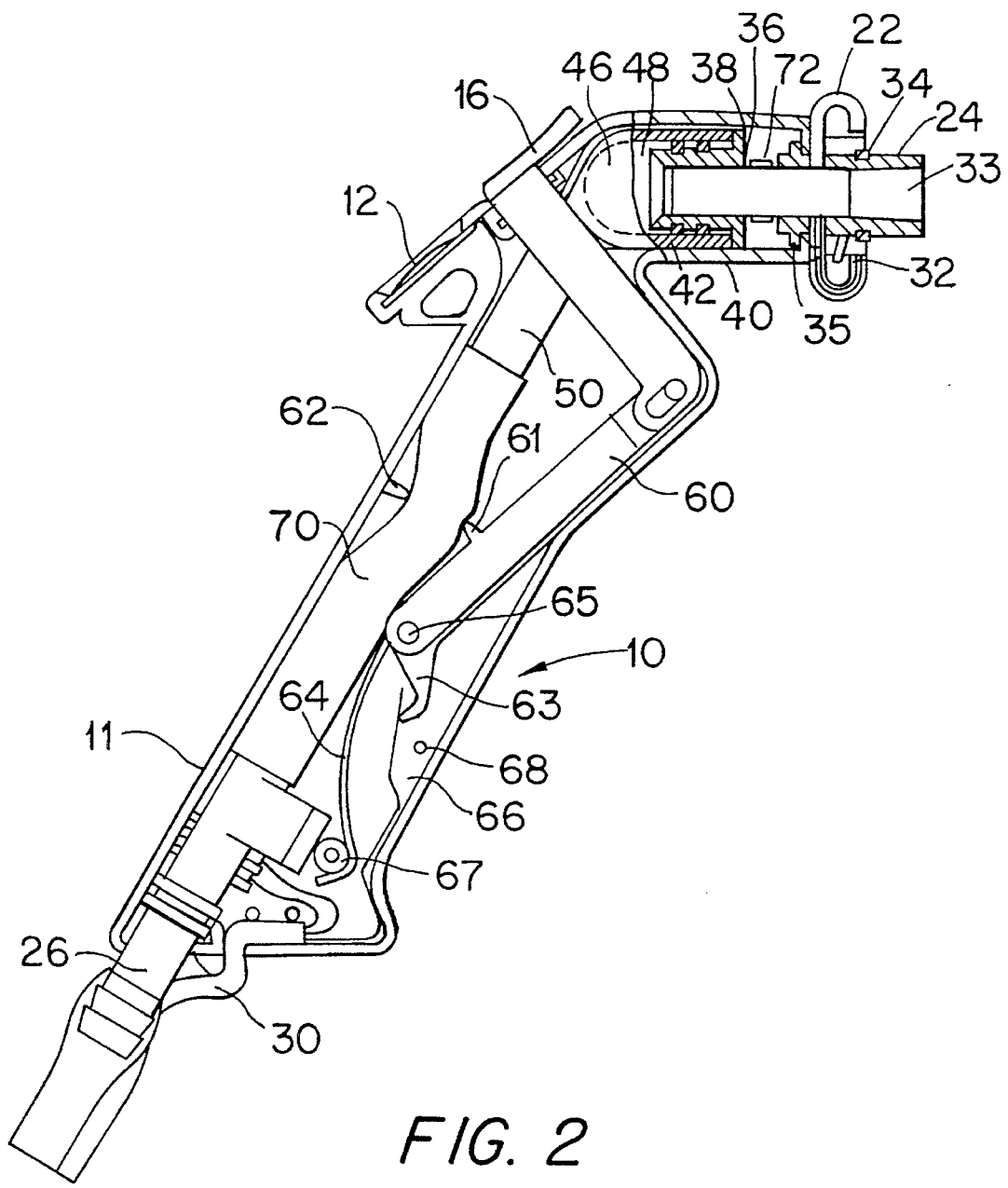
FIG. 2 is a side view of the handle assembly of the embodiment of FIG. 1 with the top half removed for clarity.
Figure 3:
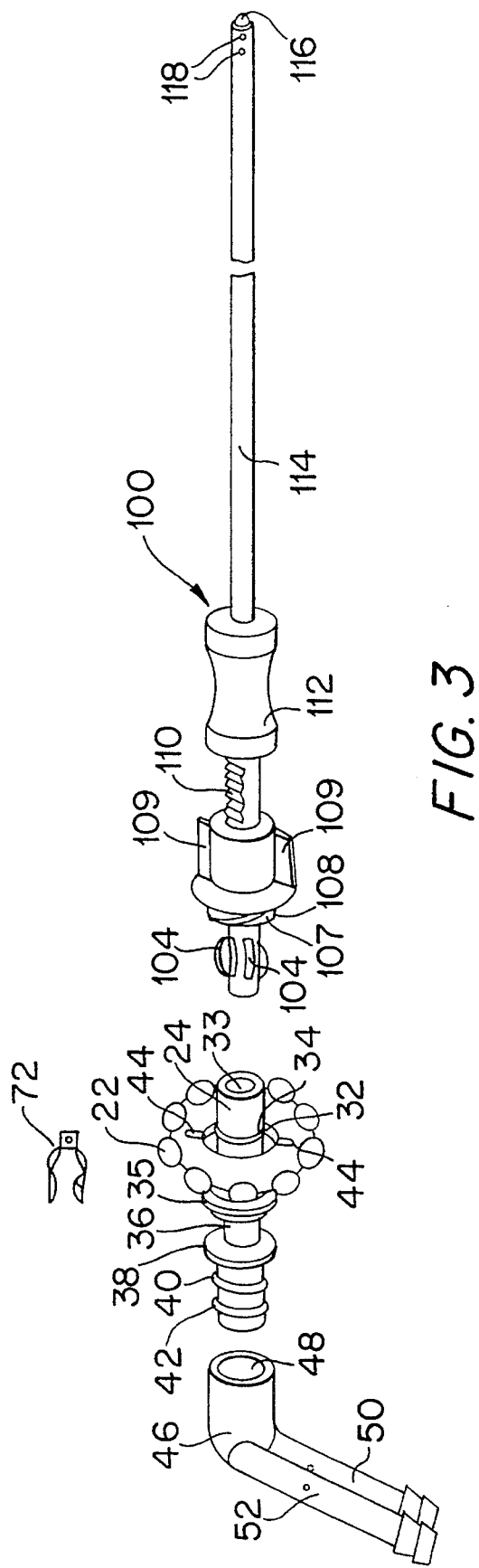
FIG. 3 shows an exploded view of a portion of the handle assembly of the embodiment of FIGS. 1 and 2.

FIG. 2 shows a side view of handle assembly 10 with the top half of handle assembly 10 (including suction button 16 and suction port 50 of manifold 46) removed for clarity and FIG. 3 shows an exploded view of a portion of handle assembly 10. With reference to these figures, instrument port 24 is shown having a center bore 33 longitudinally therethrough, O-rings 40 and 42 located toward the proximal end, in an open end cap 38, a center portion 36 made of stainless steel, a finger wheel 22, and an O-ring 34 located between finger wheel 22 and the distal end of instrument port 24. When assembled, the proximal end of instrument port 24, including end cap 38 and associated O-rings 40 and 42, fits inside port 48 of manifold 46, thus allowing leakage free communication between suction port 50 and irrigation port 52 of manifold 46 and center bore 33 of instrument port 24, while allowing rotation of instrument port 24 with respect to manifold 46. Clip 72, which is electrically connected to post 68 via a wire (not shown), is mounted to handle shell 11, surrounds and retains stainless steel center portion 36 of instrument port 24, and electrically connects center portion 36 to post 68. Clip 72 allows center portion 36 of instrument port 24 to rotate while maintaining the electrical connection.

Electrode assembly 100 is attached to handle assembly 10 by first inserting the proximal end of cannula 102, including spring connector 104, into center bore 33 of instrument port 24. O-ring 34 seals against the inner portion 105 of connector 106 and threaded portion 108 of connector 106 screws into inner portion 32 of finger wheel 22 and is tightened using wings 109, until lock-bumps 103 seat in recesses 44 of instrument port 24, thereby locking electrode assembly 100 to instrument port 24 and ensuring leakage free communication between suction port 50 and irrigation port 52 of manifold 46 and the distal end of cannula 102. The separate leafs of spring connector 104 contact the inner surface of center portion 36 effecting an efficient electrical connection between center portion 36 and electrode tip 116, and, therefore, between post 68 and electrode tip 116. To detach instrument assembly 100 from handle assembly 10, the user simply unscrews connector 106 from finger wheel 22 and pulls cannula 102 out of instrument port 24.

Figure 4:
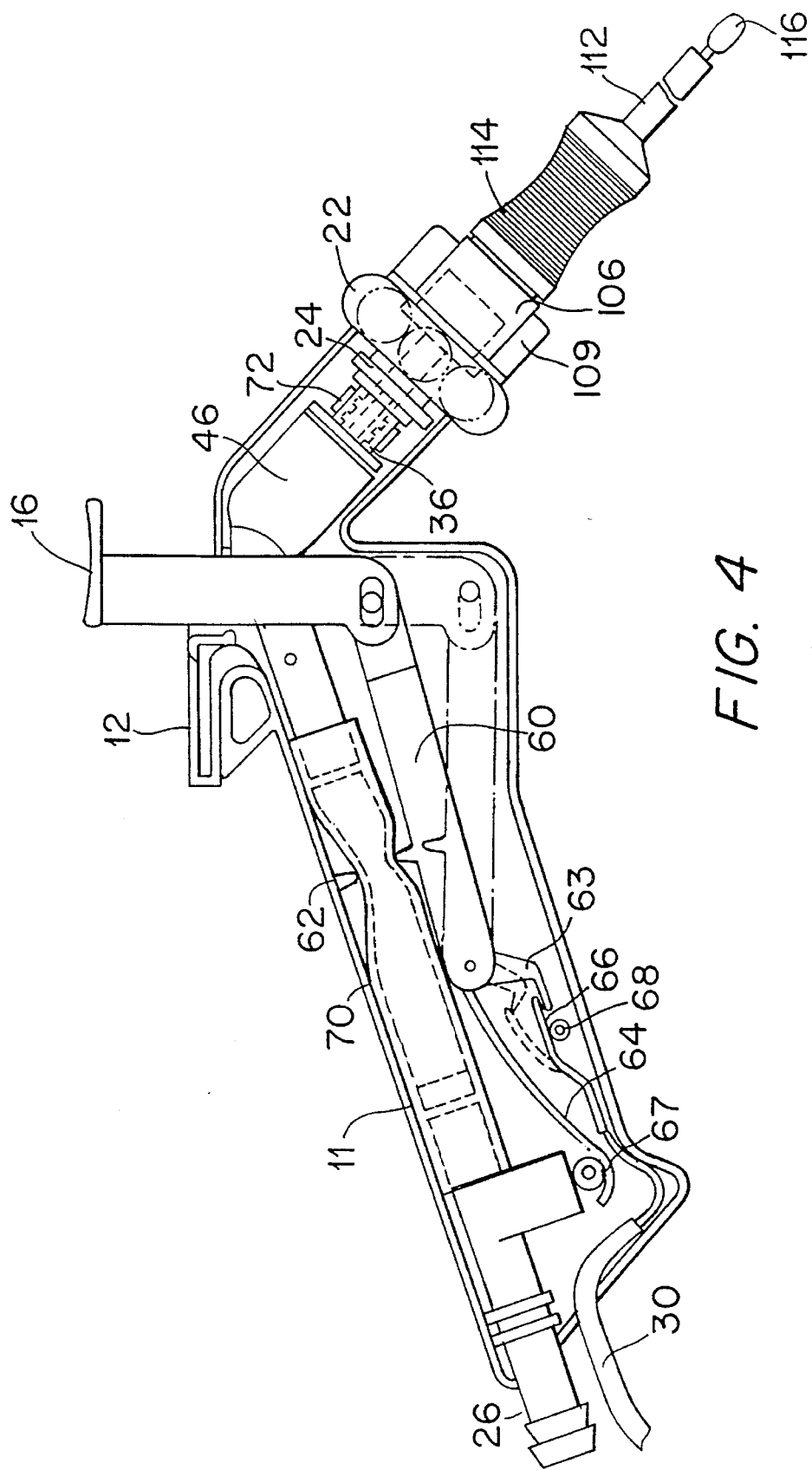
FIG. 4 shows a side view of the embodiment of FIGS. 1 and 2 with the handle assembly attached to the electrode assembly.

As shown in FIGS. 2 and 4, flexible tubing 70 connects suction port 50 of manifold 46 to suction tube 26. Not shown are irrigation port 52 of manifold 46, irrigation tube 28, the flexible tubing that connects these elements, and irrigation button 18 and its associated mechanism. Lever 60, having tab 61, arm 63, and leaf spring 64, pivots on post 65. Leaf spring 64, resting against post 67, biases lever 60 toward the upward position, shown by the solid line in FIG. 4, wherein flexible tubing 70 is pinched closed between tabs 61 and 62. When lever 60 is in this upward position, arm 63 allows spring 66, which is connected to the common conductor of cable 30, to rest against post 68, thereby completing the electrical connection between the common conductor of cable 30 and clip 72, and, therefore, also center portion 36.

When suction button 16 is depressed, as shown by the dotted lines in FIG. 4, lever 60 is moved toward the downward position, wherein tabs 61 and 62 no longer pinch flexible tubing 70 and arm 63 engages spring 66 and lifts it off of post 68, thereby breaking the electrical connection between the common conductor of cable 30 and clip 72. Irrigation button 18 has a similar mechanism (not shown in FIGS. 2 through 4) and, therefore, whenever either suction button 16 or irrigation button 18 is depressed, the associated port is in communication with instrument port 24 (and cannula 102, if attached) and no electrical current may be supplied to electrode tip 6. When the button is released, communication with the associated port is terminated and the electrical connection is reestablished.

Although the invention has been described in considerable detail with respect to preferred embodiments thereof, variations and modifications will be apparent to those skilled in the art without departing from the spirit and scope of the invention as set forth in the claims.

We claim:

1. An electrosurgical device comprising:

A handle assembly adapted to be held in the hand of a user, having a proximal side and a distal end, said handle assembly comprising:

a suction port for coupling to a suction supply;

an irrigation port for coupling to an irrigation supply;

an instrument port located on said distal end of said handle assembly and including a rotatable finger wheel for rotating said instrument port in relation to said handle assembly, said finger wheel being disposed on said distal end of said handle assembly at a location thereof such that rotation can be accomplished with a finger of the hand of a user;

suction valve means, actuated by a suction button located on said proximal side of said handle assembly so as to be depressed with the thumb of the hand of a user, for selectively providing fluid communication between said suction port and said instrument port;

irrigation valve means, actuated by an irrigation button located on said proximal side of said handle assembly so as to be depressed with the thumb of the hand of a user, for selectively providing fluid communication between said irrigation port and said instrument port;

conductor means for carrying therapeutic current, electrically coupled to said instrument port through a safety switch means, said safety switch means being actuated by depression of either said suction button or said irrigation button to decouple said conductor means from said instrument port; and current switch means, located on the proximal side of said handle assembly, for, when actuated, enabling therapeutic current to be supplied to said conductor means; and an instrument assembly detachably connected to said instrument port so as to rotate with said instrument port when said instrument port is rotated by said finger wheel.

2. An electrosurgical device as in claim 1, wherein said instrument assembly comprises an electrode tip, in electrical communication with said instrument port.

3. An electrosurgical device as claimed in claim 1 wherein said finger wheel enables rotation of said instrument port through 360°.

4. An electrosurgical device as in claim 1, wherein said instrument assembly comprises a hollow elongated cannula having a distal end and a proximal end and being in fluid communication with said instrument port.

5. An electrosurgical device as in claim 4 wherein said cannula is electrically conductive and said device further comprises an electrode tip attached to said distal end of said cannula, said cannula further being in electrical communication with said instrument port.

6. An electrosurgical device as in claim 4, further comprising:

connector means surrounding said cannula near said proximal end of said cannula, said connector means having a threaded portion extending proximally therefrom, said threaded portion being threadingly engaged with said instrument port; and a spring connector attached to said proximal end of said cannula in electrical communication with said electrode tip, said spring connector being in electrical communication with said instrument port.

7. An electrosurgical device as in claim 6, further comprising an insulating sleeve coaxially aligned with and surrounding said cannula, said insulating sleeve having an extended position in which said insulating sleeve surrounds said electrode tip, and a retracted position in which said insulating sleeve does not surround said electrode tip and said device further including means for sliding said sleeve from said extended position to said retracted position.

8. An electrosurgical device as in claim 7 wherein said means for sliding said sleeve from said extended position to said retracted position comprises a grip portion attached to said connector means, said grip portion being slidable between an extended position and a retracted position.

* * * * *